United States Patent [19]

Hsu

[11] Patent Number: 5,047,020

[45] Date of Patent: * Sep. 10, 1991

[54] IONIC HEPARIN COATING

[75] Inventor: Li-Chien Hsu, Mission Viejo, Calif.

[73] Assignee: Baxter International Inc., Deerfield, Ill.

[*] Notice: The portion of the term of this patent subsequent to Oct. 3, 2006 has been disclaimed.

[21] Appl. No.: 387,728

[22] Filed: Jul. 31, 1989

Related U.S. Application Data

[63] Continuation-in-part of Ser. No. 97,295, Sep. 14, 1987, Pat. No. 4,871,357.

[51] Int. Cl.$^5$ .............................................. A61M 5/32
[52] U.S. Cl. ................... 604/266; 604/269; 514/56; 623/1
[58] Field of Search ............................. 604/266–269; 514/56; 623/1

[56] References Cited

U.S. PATENT DOCUMENTS

| | | |
|---|---|---|
| 3,522,346 | 7/1970 | Chang . |
| 3,634,123 | 1/1972 | Eriksson et al. . |
| 3,717,502 | 2/1973 | Masuhara et al. . |
| 3,810,781 | 5/1974 | Eriksson et al. . |
| 3,835,112 | 6/1971 | Mardiguian et al. . |
| 3,853,804 | 12/1974 | Yen et al. . |
| 4,118,485 | 10/1978 | Eriksson et al. . |
| 4,254,180 | 3/1981 | Kline . |
| 4,265,927 | 5/1981 | Ericksson et al. . |
| 4,302,368 | 11/1981 | Dudley et al. . |
| 4,326,532 | 4/1982 | Hammar . |
| 4,329,383 | 5/1982 | Joh . |
| 4,331,697 | 5/1982 | Kudo et al. . |
| 4,350,806 | 9/1982 | Wagener . |
| 4,415,490 | 11/1983 | Joh . |
| 4,440,926 | 4/1984 | Mardiguian . |
| 4,565,740 | 1/1986 | Golander et al. . |

FOREIGN PATENT DOCUMENTS 8010792 5/1980 France .
5443041 10/1980 Japan .
161801 12/1980 Japan .

OTHER PUBLICATIONS

H. V. Roohk, "A Thrombogenic Index for Blood Contact Materials", vol. XXIII Trans. Am. Soc. Artif. Intern. Organa, 1977, pp. 152–161.
Thomas M. S. Chang, "Semipermeable Aqueous Microcapsules", Canadian Journal of Physiology and Pharmacology, vol. 45, 1967, pp. 705–715.
Kurt Amplatz, "A Simple Non-Thrombogenic Coating", Investigative Radiology, vol. 6, No. 4, Jul.–Aug. 1971, pp. 280–289.

Primary Examiner—Robert Bahr
Assistant Examiner—J. L. Doyle
Attorney, Agent, or Firm—Michael C. Schiffer; Bruce M. Canter

[57] ABSTRACT

A non thrombogenic quaternary ammonium-heparin complex coating for a medical article comprising an amount of at least 50% by weight of one or more cationic quaternary ammonium organic salts having the following formula:

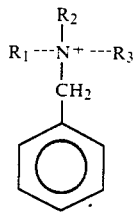

Wherein $R_1$ is an alkyl group having from about 14 to about 22 carbons;

$R_2$ is an alkyl group having from about 1 to about five carbons;

$R_3$ is an alkyl group having from about 1 to about five carbons.

32 Claims, No Drawings

IONIC HEPARIN COATING

BACKGROUND OF THE INVENTION

In recent years great advances in medical technology have produced man made materials that make direct contact with human blood. For example, medical devices must be used in temporarily conducting the blood out of the body or used as substituted artificial organs in the body thereby necessitating the devices making direct contact with blood. Such materials include by way of example, monitoring tubes, artificial kidneys, heart valves, blood by-pass tubes and dialysis membranes.

The present state of medical technology indicates that polymers, both natural and synthetic, particularly certain synthetic plastics, have come into prominence as preferred materials for prosthetic devices. It is also known that upon contact with such materials, the blood easily coagulates and forms a thrombus or a clot on the surface of such materials. The thrombus or clot creates the serious risk of blood current blockage or, alternatively, moves along with the blood flow to cause equally dangerous complications such as pulmonary thrombosis, cerebral thrombosis or myocardial infarction.

In the use of blood contacting medical devices it has always been conventional medical practice to prevent thrombus formation by systematically administering to a patient an anticoagulant agent such as heparin, coumarine, and similar compositions. However, direct and systematic administration of these anti-coagulants also increases the risks of bleeding in a subject.

Heparin is the most well known anticoagulant and a polysaccharide not having a uniform molecular structure. It is generally considered a mixture of polymers of varying size and slight differences exist between the polymers and in the individual sugars within a particular polymer grouping. It is current expert opinion that heparin is composed of alternating derivatives of D-glycocyamine (N-sulfated or N-acetylated) and uranic acid (L-iduronic acid with varying sulfate or D-glucuronic acid) joined by glycosidic linkages.

In an effort to counteract thrombogenicity and engendered bleeding, caused by direct administration of heparin, many researchers developed methods of attaching and binding heparin in the form of a coating to the walls of medical articles. Dr. Vincent Gott made the original advance in the preparation of non-thrombogenic materials by treating a graphite plastic surface with benzalkonium chloride and then with heparin. Materials treated in this way were non-thrombogenic in vitro for prolonged periods of time. Further developments followed. Two patents issued to Ericksson et al U.S. Pat. Nos. 3,810,781 and 4,118,485, where a medical article is rendered non-thrombogenic by applying a heparin coating prepared by providing a dialdehyde. Another patent issued to Eriksson et al, U.S. Pat. No. 4,265,927, issued on May 5, 1981, teaches reacting a charged surface with a colloidal aqueous solution of a cationic surface active agent and heparin. The surface active agent of choice is specifically mentioned as one of a primary amine type.

While such medical research has resulted in improved stabilization of the heparinized surface, the covalent bonding which takes place with the stabilizing dialdehyde results in reduction of the physiological activity of the heparin. Additionally, such a procedure is complicated in that many steps are involved and, consequently, is relatively costly.

One presently available heparin complex used to treat blood contacting surfaces is formed from benzalkonium chloride. This available complex is actually a mixture of alkylbenzyldimethylammonium chloride of the general formula, $[C_6H_5CH_2 N (CH_3)_2 R]Cl$, in which R represents a mixture of alkyls, including all or some of the groups comprising $C_8$ and greater, with $C_{12}$, $C_{14}$ and $C_{16}$ comprising the major portion. Generally, the composition breaks down to more than 20% $C_{14}$, more than 40%, $C_{12}$ and a less than 30% mixture of $C_8$, $C_{10}$ and $C_{16}$. The use of benzalkonium chloride is taught in U.S. Pat. No. 3,522,346, issued to Chang on July 28, 1970; and in the articles "Semipermeable Aqueous Microcapsules", Chang et al, Canadian Journal of Physiology and Pharmacology, Vol. 45, 1967, Pages 705–715; and "A Simple Non-thrombogenic Coating", Amplatz, MD, Investigative Radiology, Vol. 6, No. 4, July-August 1971, Pages 280–289. While the use of benzalkonium chloride/heparin complex coatings on medical articles has been effective, especially for short duration applications, they still demonstrate limited stability.

The binding of heparin onto a plastic polymer surface in a fully stable way has presented considerable difficulties. One major disadvantage with plastic materials coated with currently available heparin-benzalkonium complexes is that these coating complexes are unstable and subject to desorption or leaching. Consequently, in contact with biological fluids such coating can lose up to one half of the heparin content in a period of 20 minutes. The offered explanation for this phenomena is that the ionic bonding of the anionic heparin to the cationic organic quaternary ammonium groups in the plastic surface is so unstable that heparin is continuously lost with fluid flow. Only short term applications involving blood contact of short duration can be carried out with such unstable heparinized surfaces.

Other investigators have suggested using additional types of ammonium salts which are complexed with heparin. A group of surface active agents was suggested in U.S. Pat. No. 3,717,502, issued to Masuhara et al on Feb. 20, 1973. This list broadly includes dimethyl alkylbenzyl ammonium chloride, benzyldimethyl-2-[2-(p-1,1,3,4-tetramethylbutyl phenoxy) ethoxyl]ammonium chloride, alkyl-trimethylammonium chloride, dilauryldimethyammonium chloride or the like. Alkylammonium salts were suggested in U.S. Pat. Nos. 4,302,368, issued to Dudley, deceased et al on Nov. 24, 1981; and 3,634,123, and in article "A Thrombogenic Index For Blood Contacting Materials", Roohk et al, American Society Artificial Internal Organs, Vol. XXIII, 1977, page 152-161.

As demonstrated above, benzalkonium chloride/heparin complex coatings, while providing adequate biocompatibility, were not sufficiently stable in saline. Other investigators have demonstrated that some alkyl ammonium salts, e.g. tridodecylmethyl ammonium salts, do not inhibit thrombogensis.

Still other investigators have complexed heparin with esters, see U.S. Pat. No. 3,835,112, issued to Mandiguian et al on Sept. 10, 1974, U.S. Pat. No. 4,440,926, issued to Mandiguian on Apr. 3, 1984 and French Pat. No. 010792 issued on Nov. 20, 1981, to Pharmindustrie. In U.S. Pat. No. 4,326,532, issued to Hammar on Apr. 27, 1982, heparin and chitosan were reacted together to form a non-thrombogenic coating.

Still further investigators have suggested attaching heparin covalently or ionically to polymers, see U.S. Pat. Nos. 4,415,490, issued to Joh on Nov. 15, 1983; 3,853,804, issued to Yen et al on Dec. 10, 1974, 4,350,806, issued to Hagener on Sept. 21, 1982 and Japanese Patent 043041, issued to Toray Industries Inc. on Nov. 4, 1979.

Other attempts of attaching heparin to device surfaces have involved preparing the substrate surface to react with cationic or anionic compounds, e.g. heparin. In U.S. Pat. No. 4,565,740, issued to Golander et al on Jan. 21, 1986 a complex formed by treating the substrate surface with a polymeric cationic surfactant and a dialdehyde could then be subsequently reacted with cationic or anionic compounds, including heparin. U.S. Pat. No. 4,254,180, issued to Kline on Mar. 3, 1981, disclosed a mixture of a resin and colloidal graphite used to form objects. The exposed surface was made heparin recieptive by treatment with a cationic surface active agent. Derivatives of heparin have also been suggested as providing anti-thrombogenic properties. For example, in U.S. Pat. No. 4,331,697, issued to Kudo et al on May 25, 1982, a specific derivative of heparin was disclosed which in the presence of actinic light was applied to the surface of medical devices.

The above references demonstrate the keen interest in developing a heparin, or similar type reagent, biocompatible coating. However, available heparin coatings do not provide adequate saline stability or non-thrombogenic properties. Against this background it is important to find new heparin coating compositions which optimize stability, particularly in saline, and provide assured protection against thrombogensis. These compositions should be capable of being applied satisfactorily and consistently to a variety of materials such as natural polymers and synthetic plastics and will result in complete coverage of a medical article substrate surface with an adhesive film coating.

In co-pending application U.S. Ser. No. 097,295, filed on Sept. 14, 1987, which is a continuation of U.S. Ser. No. 820,670 non-thrombogenic quaternary ammonium/heparin complexes were disclosed. These complexes were demonstrated as providing improved saline stability and biological activity over previously disclosed heparin materials. These disclosed complexes were alkylbenzyldimethyl ammonium cationic ions having the formula:

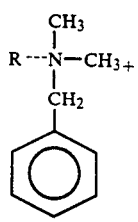

Where R is a uniform alkyl group containing between 16 to 18 carbon atoms.

The present invention relates to additional alkylbenzyl ammonium/heparin complexes useful as coating composition having improved surface adhesion and anti-thrombogenic than heparin compositions heretofore known. These compositions have the distinct advantages of being relatively simple to prepare and easily applied as coatings to medical article surfaces.

SUMMARY OF THE INVENTION

In accordance with the present invention non-thrombogenic quaternary ammonium/heparin complexes are provided having in excess of fifty percent by weight of one or more alkylbenzyl ammonium cationic ions having the formula:

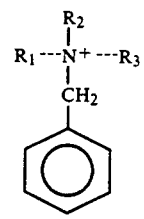

Wherein
$R_1$ is an alkyl group having from about 14, 15 or 19 to about 22 carbons;
$R_2$ is an alkyl group having from about 1 to about five carbons; and
$R_3$ is an alkyl group having from about 1 to about five carbons;

Additionally, methods are provided for preparing the present complex and rendering the surface of a medical article non-thrombogenic. These processes either involve coating the surface of such a device with the present trialkylbenzyl ammonium-heparin complex, or coating the surface with a representative trialkylbenzyl ammonium salt and subsequently treating this surface with heparin salt.

As will be discussed in detail below, surfaces of medical articles so treated with the instant heparin complex have prolonged non-thrombogenicity, improved adhesion to polymer surfaces, decreased desorption and improved biological compatibility.

DETAILED DESCRIPTION OF THE INVENTION

As indicated above, the present invention relates to a hydrophobic, organic solvent soluble coating complex comprising anionic heparin and at least 50% by weight of one or more alkylbenzyl ammonium cationic salts of the following formula:

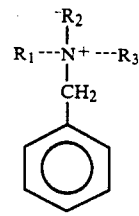

Wherein
$R_1$ is an alkyl group having from about 14 to about 22 carbons;
$R_2$ is an alkyl group having from about 1 to about five carbons; and,
$R_3$ is an alkyl group having from about 1 to about five carbons.

In the above referred to co-pending application U.S. Ser. No. 097,295, the alkylbenzyl ammonium cationic salts consisted of those wherein $R_1$ is an alkyl group having from about 16 to about 18 carbons, while $R_2$ and $R_3$ are methyl groups. It has now been determined that additional trialkylbenzyl ammonium cationic salts are useful for the purposes of the present invention. These cationic salts are of the formula:

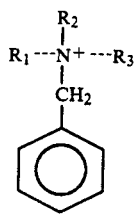

Wherein
R₁ is an alkyl group having from about 14, 15 or 19 to about 22 carbons;
R₂ is an alkyl group having from about 1 to about five carbons; and
R₃ is an alkyl group having from about 1 to about five carbons.

When medical articles are coated with the instant heparin complex they are found to have the following characteristics when compared with presently used heparin coatings:
(1) improved adhesion and surface retention:
(2) prolonged non-thrombogenicity and decreased desorption; and
(3) optimum hydrophobicity and solubility in organic solvents.

The invention also provides a process for coating the surface of polymeric medical articles comprising:
(a) providing a medical article; and
(b) coating the medical article with a complex of anionic heparin and at least 50% by weight of one or more alkylbenzyl ammonium cationic salts of the following formula:

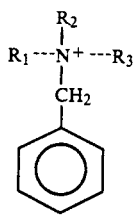

Wherein
R₁ is an alkyl group having from about 14 to about 22 carbons;
R₂ is an alkyl group having from about 1 to about five carbons; and
R₃ is an alkyl group having from about 1 to about five carbons.

With a first group of such cationic salts being those wherein R₁ is an alkyl group having from 16 to 18 carbons, with R₂ and R₃ being methyl groups, and a second group of such cationic salts being those wherein R₁ is an alkyl group having from about 14, 15 or 19 to about 22 carbons; R₂ is an alkyl group having from about 1 to about five carbons; and R₃ is an alkyl group having from about 1 to about five carbons.

In accordance with another embodiment the process is carried out by treating the medical article with a solution of at least 50% by weight of one or more cationic quaternary ammonium organic salts having the following formula:

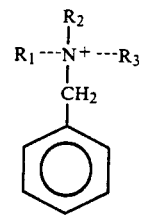

Wherein
R₁ is an alkyl group having from about 14, 15 or 19 to about 22 carbons;
R₂ is an alkyl group having from about 1 to about five carbons;
R₃ is an alkyl group having from about 1 to about five carbons; and
X is a halogen; and
applying a heparin salt to such treated surface.

The process of the instant invention further includes direct coating means of the heparin complex by straight application means as in the case of dip coating and indirect coating means as in the case of sequential applications of a cationic salt surfactant and the ionic heparin.

As is evident from the above description, there is provided a particular heparin/quaternary ammonium complex which when applied to the surface of medical articles results in a markedly improved heparinized coating. Of critical importance is the discovery herein of particular alkylbenzyl dimethyl ammonium cationic salts which can be used in high loading concentrations with heparin to form coatings having the stated beneficial features. It has been found that the present heparin/quaternary ammonium complex must have at least 50 weight percent of the organic cationic salt and preferably from 60 to 70 weight percent to achieve medical article coatings of optimum quality. Height percent as used herein means the ratios of the quaternary ammonium moieties to the total weight of the complex. These weight percentages relate to, but are not limited by, the degrees of substitution of the heparin molecule by the cationic quaternary ammonium salt.

While all the present heparin complexes and mixtures thereof have the desired non-thrombogenic and stability characteristics, optimum and preferred results have been achieved with complexes consisting of cetalkonium heparin and/or stearylkonium heparin and mixtures thereof. It appears that the homogeneous nature of the organic cationic salt gives optimum stability and uniformity to the ultimate coating.

While not to be construed as limiting, it is speculated that the unexpected results achieved with the instant heparin/quaternary ammonium complex in conjunction with organic substrate surfaces result from the use of the particular organic salts at high concentrations. Therefore it is theorized that the longer organic chains of the cationic salt cause greater affinity to the organic substrate surface and their high concentration enhances the adhesion of the complex thereby stabilizing the heparin on the organic surface. Consequently the instant complex coating has vastly superior hydrophobicity and surface adhesion over the presently and most commonly used complexes of heparin and benzalkonium chloride.

Commercially available Benzalkonium Chloride is a mixture of alkylbenzyldimethylammonium chloride of the general formula, [C₆H₅CH₂ N (CH₃)₂ R]Cl, in which R represents a mixture of alkyls, including all or some of the groups comprising $C_8$ and greater, with $C_{12}$, $C_{14}$ and $C_{16}$ comprising the major portion. Generally, the composition breaks down to more than 20% $C_{14}$, more than 40%, $C_{12}$ and a less than 30% mixture of $C_8$, $C_{10}$ and $C_{16}$. While the use of benzalkonium chloride/heparin complex coatings on medical articles has been effective, especially for short duration applications, they still demonstrate limited stability which is probably due to the heterogeneous nature of the mixture.

Any conventional material which makes direct contact with the blood such as glass, metals, and resins may be used as substrates within the purview of the present invention. The polymeric resin materials which serve as the substrate to be treated by the composition and processes of this invention may be any polymeric resin, natural or synthetic, conventionally used to fabricate articles commonly used in contact with blood. For example, catheters, artificial blood vessels, valves and like prosthetics are frequently fabricated from a polyethylene, polyacrylic, polypropylene, polyvinyl chloride, polyamide, polyurethane, polyvinylpyrrolidone, polyvinyl alcohol, cellulose acetate, polystyrene, polytetrafluoroethylene, polyester such as polyethylene terephthalate, silicone rubber, natural rubber, polycarbonate and like polymeric resins and hydrogels, thereof. The resin substrate may be rigid or flexible in character, cellular or non-cellular, porous or non-porous. Also within the scope of the invention is the treatment of a coating of such a polymer resin on a metal or ceramic material.

The following examples give greater illustration and understanding of the invention.

In the first set of examples (Examples 1-3) are directed to the alkylbenzyl dimethyl ammonium cationic salts wherein $R_1$ is an alkyl group having from about 16 to 18 carbons, with $R_2$ and $R_3$ being methyl groups. These examples demonstrate the improved stability and biocompatibility of this case of compounds, of which ammonium cationic salts of the instant invention are a part, in comparison to presently available compounds and compositions.

EXAMPLE 1

A Stearyl dimethyl benzyl ammonium Heparin complex was prepared as follows: 27 grams of heparin was dissolved in 215 milliliters of distilled water. The solution was mixed with a 420 milliliter of a water solution containing 63 grams of purified Stearyl dimethyl benzyl ammonium chloride. This mixing was performed by stirring the heparin solution and adding the stearylkonium chloride solution to it in a drop wise manner whereby an insoluble complex of heparin and the stearylkonium chloride was formed as a precipitate. This complex compound was separated from solution by means of filtration and found to contain about 63% stearylkonium cation. The complex was found to be highly hydrophobic and had limited solubilities in polar organic solvents such as methanol, ethanol and isopropyl alcohol.

EXAMPLE 2

To illustrate the comparative characteristics of the heparin complex prepared in Example 1 and benzalkonium heparin, which is a presently available compound, the following example and tests were carried out. Six polyester cores generally used in arterial filters known as AF 1025 and manufactured by American Hospital Supply Corporation were provided. Two are dip coated in a 0.2%, by weight of commercially available benzalkonium heparin ("BKH") dissolved in isopropyl alcohol. Two other cores were dip coated in a 0.2%, by weight solution of stearylkonium heparin ("SKH") dissolved in a mixture of trifluro trichloro ethane and ethanol. The two remaining cores were tested as controls.

The prepared filters along with the controls were subjected to a leaching or desorption test to determine the amount of heparin loss experienced with circulating saline liquid. The amounts and the biological activities of the respective heparin complexes on each filter were determined. The quantity of the heparin complex was ascertained by extraction with an organic solvent and the extract subjected to ultraviolet spectrophotometric analysis. The heparin biological activity test was performed utilizing a different portion of the same extracts in accordance with the Propopath Proteolytic Enzyme Detection System of American Hospital Supply Corporation.

The leaching test was carried out as follows. The saline circulation text utilized $\frac{3}{8}'' \times 3/32''$ PVC tubing of three meters in length, a total saline volume of 1.5 liters, and the test was run at a temperature of 37° C. The saline solution was continuously circulated through the test circuit and saline samples were removed at predetermined intervals. These samples were analyzed for heparin content and activities as indicated above.

After 4 hours of saline circulation, each filter was removed and dissected. 250mls. of ethyl alcohol was then used to extract any organic coatings on the core of each filter including the control. The alcohol extract was then subjected to the UV spectrophotometric test to determine the amount of heparin complex as well as the biological activity test indicated above. The amounts and activities of heparin complexes remaining on the two sets of filters before and after saline leaching are tabulated in Tables 1 and 2. The intermittent activities of the respective saline solutions are outlined in Table 3.

Turning to Tables 1 and 2, it is evident that the Stearylkonium Heparin coating is more stable than the Benzalkonium Heparin because in excess of 80% of the original SKH coating composition survives the saline leaching in both sets of tests whereas there is a loss of at least 85% of the BKH coatings. This is confirmed by the Heparin Activity test of the residual coatings which indicates that BKH loses a minimum of 75% of its heparin activity over the four hours of saline leaching.

The test date of Tables 1 and 2 are also important because medical devices used for blood flow are generally primed or stored in saline solutions.

Consequently desorption characteristics in this medium are important in and of themselves. As one example, blood gas sensor devices used for determining types and amounts of blood gases are generally coated with heparin complexes and stored in saline. It can be appreciated from the test data that such devices coated with benzalkonium heparin will not have the requisite antithrombogenic quality after significant saline storage.

TABLE 1

FIRST SET

|  | BEFORE SALINE RECIRCULATION | | AFTER 4 HRS. OF SALINE RECIRCULATION | |
| --- | --- | --- | --- | --- |
|  | mg BKH or SKH | HEPARIN ACTIVITY | mg BKH or SKH | HEPARIN ACTIVITY |
| 0.2% BKH COATED FILTER | 19 | 1140 | 0 (0% OF ORIGINAL) | 122 (10.7% OF ORIGINAL) |
| 0.2% SKH COATED FILTER | 19 | 875 | 16.3 (85.7% OF ORIGINAL) | 750 (85.7% OF ORIGINAL) |

TABLE 2

SECOND SET

|  | BEFORE SALINE RECIRCULATION | | AFTER 4 HRS. OF SALINE RECIRCULATION | |
| --- | --- | --- | --- | --- |
|  | mg BKH or SKH | HEPARIN ACTIVITY | mg BKH or SKH | HEPARIN ACTIVITY |
| 0.2% BKH COATED FILTER | 19 | 1140 | 2.3 (12.1% OF ORIGINAL) | 271 (23.8% OF ORIGINAL) |
| 0.2% SKH COATED FILTER | 19 | 875 | 16.0 (84.2% OF ORIGINAL) | 750 (85.7% OF ORIGINAL) |

Table 3 outlines the time interval readings of the heparin activities of the circulating solutions. There is no detection (ND) of biological heparin activity during the SKH test while the BKH demonstrates an accelerated desorption within the first hour and virtual deactivation over the four hour period. This data confirms the conclusions reached with respect to Tables 1 and 2.

TABLE 3

TOTAL HEPARIN ACTIVITY DETECTED IN CIRCULATING SALINE

|  | 0.2% BKH COATED FILTER | 0.2% SKH COATED FILTER |
| --- | --- | --- |
| 0 TIME (AFTER PRIMING) | 240 | ND |
| 1 HOUR | 698 | ND |
| 2 HOURS | 765 | ND |
| 3¼ HOURS | 788 | ND |
| 4 HOURS | 788 | ND |

The following demonstrates the non-thrombogenic nature of SKH.

EXAMPLE 3

Fibrinogen adsorption is a known precursor to thrombogenesis. Therefore by comparing relative amounts of Fibrinogen bound by different surfaces, predictions can be formulated on the relative thromboginicity of an artificial blood contact material. This methodology utilizes a radiolabeled Fibrinogen which is dynamically exposed to a surface with a phosphate buffer carrier. Then by determining the radioactivity of the test samples, a relative amount of bound Fibrinogen can be determined. The Fibrinogen Adsorption Test is outlined by H. V. Roohk et al, Vol. XXIII *Tran. Am. Soc. Art. Interm Organs.* 1977, pg. 157 herein incorporated by reference. This method can be utilized as an index to evaluate and screen artificial blood contact surfaces for blood compatibility.

A medical grade PVC tubing is dip coated in 0.4% (WT/volume) SKH in a mixture of Trichloro-trifluro ethane and ethanol, subsequently dried, and sterilized by gamma radiation. The tubing sample and a control PVC tubing sample is then subjected to the Fibrinogen Adsorption Test of Roohk et al and the results set forth in Table 4. As can be appreciated there is increasing fibrinogen adsorption on the control over time and minimal Fibrinogen adsorption on the SKH coated PVC thereby demonstrating the excellent anti-thrombogenic nature of the SKH coatings of the present invention.

TABLE 4

PERCENTAGE OF FIBRINOGEN ADSORPTION

| TIME CONTROL | PVC TUBING | SKH COATED PVC TUBING |
| --- | --- | --- |
| 0 | 0.00 | 0.00 |
| 30 min | 0.48 | 0.22 |
| 60 min | 0.69 | 0.20 |
| 90 min | 0.74 | 0.22 |

In summary, the results of the examples and the data of tables 1–4, indicate that stearylkonium/heparin (SKH) complex coatings have the following properties:

1. Superior surface adhesion in that SKH is 10 times less soluble in saline than benzalkonium heparin complex and is more hydrophobic and has higher affinity to plastic surfaces than benzalkonium heparin complex.

2. Nonflammable solvent solubility (e.g. freon TE-35), because of the high loading of detergent thereby rendering the complex virtually non polar.

3. Improved anti-thrombogenic performance to that of BKH.

EXAMPLE 4

Example 4 demonstrates the stability of the group of trialkylbenzyl ammonium heparin wherein $R_1$ is an alkyl group having from about 14, 15 or 19 to 22 carbons; $R_2$ is an alkyl group having from about 1 to five carbons; and $R_3$ is an alkyl group having from about 1 to five carbons. of the invention on artificial surfaces. As stated above, the ability of the heparin salts of the invention to provide an improved biocompatible surface is dependent upon the capability of the salt to remain on the surface. This capability is demonstrated by the following example.

Six quaternary ammonium salts were used in preparation of the heparin complexes. These complexes were prepared in accordance with those procedures described for the preparation of the stearyl dimethyl benzyl ammonium heparin complex in Example 1. The ammonium salts used in the preparation of the heparin complexes were:

Myristyl dimethyl ($R_1 = C_{14}$, and $R_2$ and $R_3 =$ are $C_1$) benzyl ammonium chloride;

Eicosane dimethyl ($R_1 = C_{20}$, and $R_2$ and $R_3 =$ are $C_1$) benzyl ammonium chloride..

Docosane dimethyl ($R_1 = C_{22}$, and $R_2$ and $R_3 =$ are $C_1$) benzyl ammonium chloride;

Stearyl dipentyl ($R_1 = C_{18}$, and $R_2$ and $R_3 =$ are $C_5$) benzyl ammonium chloride;

Stearyl dibutyl ($R_1 = C_{18}$, and $R_2$ and $R_3 =$ are $C_4$) benzyl ammonium chloride; and Stearyl methyl butyl ($R_1 = C_{18}$, $R_2 = C_1$ and $R_3 = C_4$) benzyl ammonium chloride.

The blood contacting surfaces of an arterial blood filter were flashed coated by passing a 0.25% weight-/volume solution of the prepared quaternary ammonium heparin complexes dissolved in a mixture of trifluorotrichloroethane and ethanol or toluene through the filter. The filter was then air dried. The filter used was an arterial filter known as AF 1040 or 540 sold and manufactured by Baxter Healthcare Corporation of Deerfield, Illinois. Filters were also coated with a 0.25% weight/volume solution of Benzalkonium heparin complex in isopropyl alcohol. This later complex is, as already stated, a commercially available complex. The results of a comparison of the stability of this later complex with those of the invention demonstrate the unexpected benefits of the invention.

The coated filters were subjected to a saline recirculation procedure similar to that described in Example 2. The saline recirculation conditions varied by flowing the saline through the filters at a rate of 4 liters/minute, under ambient temperature for a total of 2 hours.

After completion of the saline recirculation the concentration of the heparin on the blood contacting surfaces was determined by a Factor Xa Inhibition Assay. This assay is described in greater detail in U.S. Pharmacopeia National Formulary, 1985 Edition (21st Revision of U.S. Pharmacopeia, 16th Edition National Formulary) at page 482 of the Official Monographs under the subject heading "Heparin Sodium", which is incorporated in its entirety herein. The described assay procedure requires the use of a chromophore substrate. The assays performed in this Example used a chromogenic substrate, model number F-2222 manufactured by the Kabi Vitrum A.B., Diagnostica Company of Sweden.

The results of this assay are listed below in Table 5.

TABLE 5

| HEPARIN COMPLEX | AMOUNT OF HEPARIN BEFORE SALINE LEACHING[1] | AMOUNT OF HEPARIN RETAINED AFTER SALINE LEACHING[1] |
| --- | --- | --- |
| Myristyl dimethyl benzyl heparin | 479 n = 2 | 499 (100% retention) n = 2 |
| Eicosane dimethyl benzyl heparin | 779 n = 2 | 877 (100% retention) n = 2 |
| Docosane dimethyl benzyl heparin | 800 n = 2 | 716 (90% retention) n = 2 |
| Stearyl dipentyl benzyl heparin | 238 n = 2 | 308 (100% retention) n = 2 |
| Stearyl dibutyl benzyl heparin | 363 n = 2 | 360 (100% retention) n = 2 |
| Stearyl methyl butyl benzyl heparin | 527 n = 2 | 523 (100% retention) n = 2 |
| Benzalkonium heparin | 951 n = 2 | 210 (22% retention) n = 2 |

[1](Units = As specified in the incorporated herein reference for measuring Heparin Activity) (n = # filters tested)

In summary, the results of Example 4, as demonstrated by the data in table 5 indicates that alkyl benzyl ammonium/heparin complex coatings of this invention are substantially the same as those described in the copending application, and exemplified by the above examples 1-4. In particular the results of Example 4 demonstrate that the complexes of the invention have superior surface adhesion and are less soluble in saline than Benzalkonium heparin complex. The complexes of the invention are also more hydrophobic and have a higher affinity to plastic surfaces than Benzalkonium heparin complexes.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed:

1. A blood contacting medical article comprising:
   a. a substrate surface; and
   b. an anti-thrombogenic surface coating of a complex of heparin and at least 50% by weight of a cationic trialkylbenzyl ammonium salt having the following formula:

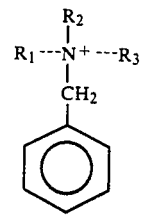

wherein $R_1$ is an alkyl group having from about 14 to about 22 carbons;
$R_2$ is an alkyl group having from about 1 to about five carbons; and
$R_3$ is an alkyl group having from about 1 to about five carbons.

2. The medical article of claim 1 wherein the complex is Myristyl dimethyl benzyl ammonium/heparin.
3. The medical article of claim 1 wherein the complex is Eicosane dimethyl benzyl ammonium/heparin.
4. The medical article of claim 1 wherein the complex is Docosane dimethyl benzyl ammonium/heparin.
5. The medical article of claim 1 wherein the complex is Stearyl dipentyl benzyl ammonium/heparin.
6. The medical article of claim 1 wherein the complex is Stearyl dibutyl benzyl ammonium/heparin.
7. The medical article of claim 1 wherein the complex is Stearyl methyl butyl benzyl ammonium/heparin.
8. The medical article of claim 1 wherein the substrate surface comprises a polymeric resin.
9. The medical article of claim 1 wherein the organic cationic salt is present in an amount of 60 to 70% by weight of the complex composition.
10. The medical article of claim 1 wherein $R_1$ is an alkyl group having about 14 carbons.
11. The medical article of claim 1 wherein $R_1$ is an alkyl group having about 15 carbons.
12. The medical article of claim 1 wherein $R_1$ is an alkyl group having from about 16 to about 18 carbons.
13. The medical article of claim 1 wherein $R_1$ is an alkyl group having from about 19 to about 22 carbons.
14. The medical article of claim 1 wherein $R_2$ is an alkyl group having from about 2 to about 5 carbons.
15. The medical article of claim 1 wherein $R_3$ is an alkyl group having from about 2 to about 5 carbons.
16. A process for rendering the surfaces of blood contacting medical articles non-thrombogenic comprising.
   a. providing a medical article; and b. coating the medical article with a complex of heparin and at least 50% by weight of one or more trialkylbenzyl dimethyl ammonium cationic salt of the formula:

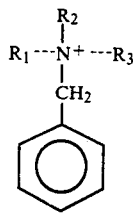

wherein $R_1$ is an alkyl group having from about 14 to about 22 carbons;

$R_2$ is an alkyl group having from about 1 to about five carbons; and $R_3$ is an alkyl group having from about 1 to about five carbons.

17. The process of claim 16 wherein the coating step comprises:
   a. providing an organic solution of the heparin complex;
   b. applying the solution to the surface of a medical article; and
   c. drying the medical article to form an integral adhesive coating thereon.

18. The process of claim 16 wherein $R_1$ is an alkyl group having about 14 carbons.

19. The process of claim 16 wherein $R_1$ is an alkyl group having about 15 carbons.

20. The process of claim 16 wherein $R_1$ is an alkyl group having from about 16 to about 18 carbons.

21. The process of claim 16 wherein $R_1$ is an alkyl group from about 19 to about 22 carbons.

22. The process of claim 16 wherein $R_2$ is an alkyl group having from about 2 to about 5 carbons.

23. The process of claim 16 wherein $R_3$ is an alkyl group having from about 2 to about 5 carbons.

24. A process for rendering the surfaces of blood contacting medical articles non-thrombogenic comprising:

a. providing a medical article; and
b. treating the medical article with a solution of at least 50% by weight of one or more trialkylbenzyl cationic quaternary ammonium organic salts having the following formula:

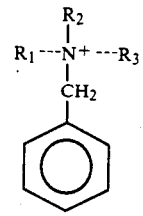

wherein $R_1$ is an alkyl group having from about 14, 15 or 19 to about 22 carbons;

$R_2$ is an alkyl group having from about 1 to about five carbons;

$R_3$ is an alkyl group having from about 1 to about five carbons; and

X is a halogen; and c. subsequently treating the medical article with an aqueous solution of heparin salt.

25. The process of claim 24 wherein the organic cationic salt consists of an alkyl $R_1$ group of 16 carbon atoms.

26. The process of claim 24 wherein the organic cationic salt consists of an alkyl R group of 18 carbon atoms.

27. The process of claim 24 wherein $R_1$ is an alkyl group having about 14 carbons.

28. The process of claim 24 wherein $R_1$ is an alkyl group having about 15 carbons.

29. The process of claim 24 wherein $R_1$ is an alkyl group having from about 16 to about 18 carbons.

30. The process of claim 24 wherein $R_1$ is an alkyl group having from about 19 to about 22 carbons.

31. The process of claim 24 wherein $R_2$ is an alkyl group having from about 2 to about 5 carbons.

32. The process of claim 24 wherein $R_3$ is an alkyl group having from about 2 to about 5 carbons.

* * * * *